United States Patent [19]

Klasen et al.

[11] Patent Number: 5,804,423
[45] Date of Patent: Sep. 8, 1998

[54] MICROBIOLOGICAL METHOD OF MAKING 5-KETOGLUCONATE

[75] Inventors: Ralf Klasen, Leverkusen; Stephanie Bringer-Meyer; Hermann Sahm, both of Jülich; Cornelies Petrus Hollenberg, Düsseldorf, all of Germany

[73] Assignees: Forschungszentrum Julich GmbH, Julich; Rhein Biotech GmbH, Dusseldorf, both of Germany

[21] Appl. No.: 594,808

[22] Filed: Jan. 31, 1996

[30] Foreign Application Priority Data

Feb. 7, 1995 [DE] Germany .................. 195 03 946.7

[51] Int. Cl.⁶ .............................. C12P 7/60; C12N 9/02; C12N 1/20; C07H 21/04
[52] U.S. Cl. ................. 435/138; 435/189; 435/252.3; 435/320.1; 536/23.8
[58] Field of Search ................ 435/25, 41, 69.1, 435/143, 189, 138, 252.3, 320.1; 536/23.2

[56] References Cited

U.S. PATENT DOCUMENTS 4,788,135  11/1988  Davis et al. ................. 435/6

OTHER PUBLICATIONS

Adachi et al. (1979) Agric. Biol. Chem. 43, 75–83.

Weenk et al. (1984) Appl. Microbiol. Biotechnol. (1984) 20, 400–405.

*Primary Examiner*—Dian C. Jacobson
*Assistant Examiner*—Elizabeth Slobodyansky
*Attorney, Agent, or Firm*—Herbert Dubno; Jonathan Myers

[57] ABSTRACT

A method is disclosed for preparing 5-ketogluconate, which comprises the steps of:

(a) genetically modifying a microorganism capable of microbiologically producing 5-ketogluconate to increase gluconate $NADP^+$-5-oxidoreductase gene expression of said microorganism;

(b) culturing said microorganism in a medium to produce 5-ketogluconate; and (c) recovering 5-ketogluconate from said medium.

12 Claims, 1 Drawing Sheet

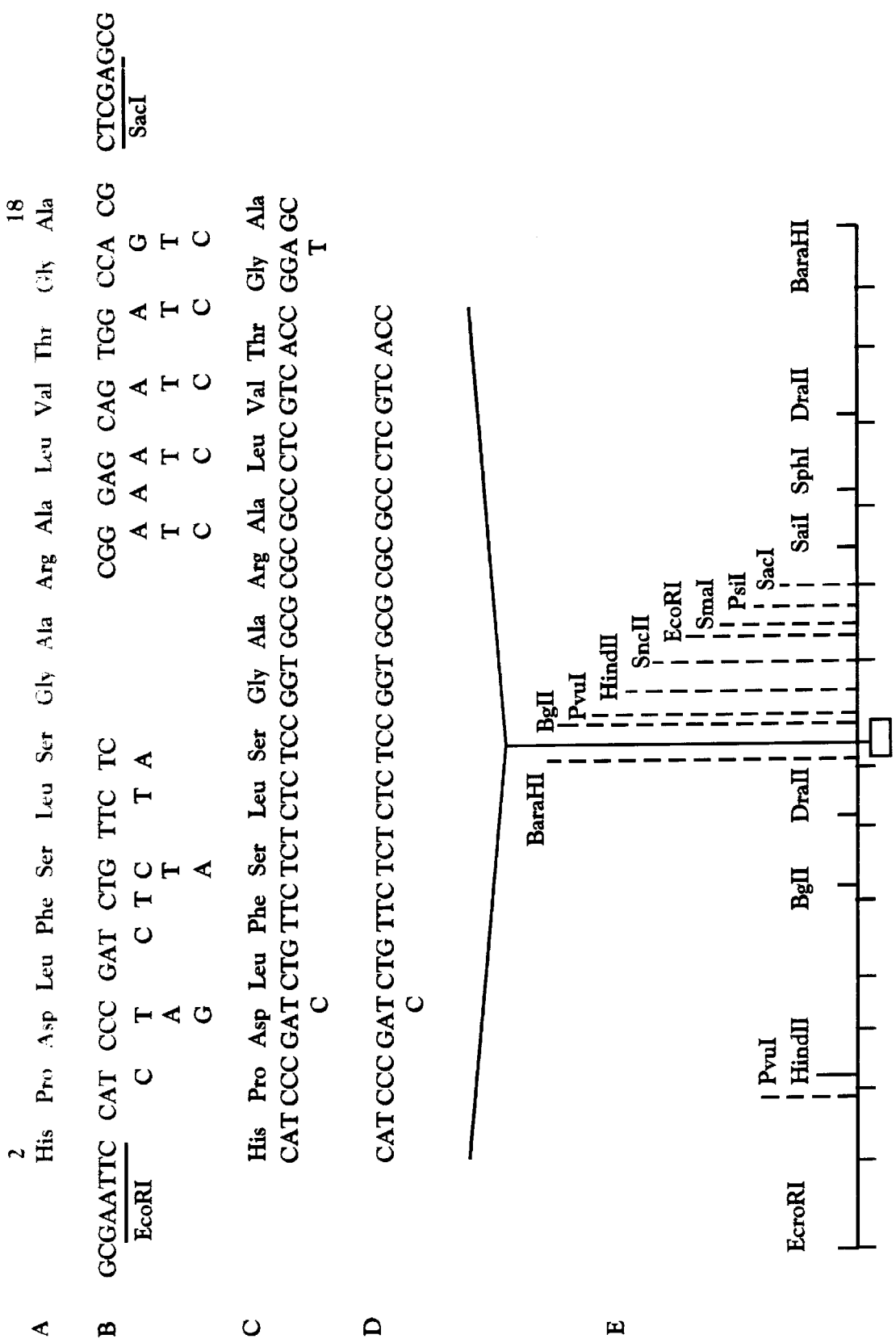

MICROBIOLOGICAL METHOD OF MAKING 5-KETOGLUCONATE

FIELD OF THE INVENTION

Our present invention relates to a microbiological method of making 5-ketogluconate, a gluconate:NADP$^+$-5-oxidoreductase gene, a gene structure containing the gluconate:NADP$^+$-5-oxidoreductase gene, a vector containing the new gluconate:NADP$^+$-5-oxidoreductase gene or gene structure, and a cell transformed to contain the new gluconate:NADP$^+$-5-oxidoreductase gene or gene structure in a replicatable form.

BACKGROUND OF THE INVENTION

It is known that certain bacteria, like for example, Gluconobacter bacteria, can oxidatively convert glucose to gluconate and gluconate further to 5-ketogluconate which can be recovered from the culture medium.

Microbial production and recovery of 5-ketogluconate is of interest for the production of ascorbic acid and especially for L-(+)-tartaric acid production. Currently the L-(+)-tartaric acid is primarily produced from tartar arising as a byproduct of wine-making. As a result the tartaric acid production is dependent upon the availability of this raw material. The raw tartar (argol) is generally also contaminated with organic materials so that the recovery of tartaric acid can require expensive processing.

Because of these drawbacks, alternative processes for the production of tartaric acid have been sought. One alternative process is the conversion of microbially produced 5-ketogluconate to the L-(+)-tartaric acid (cf. German patent document 44 40 191). However for economical practice of this process the yields of microbially produced 5-ketogluconate using earlier techniques have proved to be too low.

Gluconobacter oxydans cultured on glucose substrate can form 2-ketogluconate and 5-ketogluconate with different strain-specific yields. For the 2-ketogluconate formation, yields in the range of 4% to 97% and for the 5-ketogluconate yields of 4% to 35%, based upon converted glucose, have been described (Weenk, G., Loijve, W., and Harder, W., 1984, Ketogluconate Formation by Gluconobacter Species, *Appl. Microbiol. Biotechnol.* 20: 400–405). Different culture conditions determine which of the two ketogluconates will be produced. Thus, with a pH value of 4, an incubation temperature of 25° C. and titration with CaCO$_3$ leads to increased 5-ketogluconate production (Stadler-Szöke, A., Nyeste, L., and Hollo, J., 1980, Studies on the Factors Effecting Gluconic acid and 5-ketogluconic acid formation by Acetobacter. *Acta Aliment.* 9: 155–172), while higher pH values and higher temperatures favor the 2-ketogluconate formation (Amenyama, M., and Kondo, K., 1958, Carbohydrate Metabolism by Acetobacter Species. *Bull. Agric. Chem. Soc.* Japan, 22: 373–379).

OBJECTS OF THE INVENTION

It is thus an object of the invention to provide an improved microbiological method of making 5-ketogluconate such that the yield of the 5-ketogluconate and the proportion thereof in the products made is increased.

Another object of the invention is to provide an improved material for use in a microbiological method of making 5-ketogluconate.

Yet a further object is to provide a new gluconate:NADP$^+$-5-oxidoreductase gene.

It is also an object of the instant invention to provide, as a new species, a gene structure containing the gluconate:NADP$^+$-5-oxidoreductase gene.

Last, but not least, it is an object of the invention to provide a novel vector containing the new gluconate:NADP$^+$-5-oxidoreductase gene or gene structure, and a cell transformed to contain the new gluconate:NADP$^+$-5-oxidoreductase gene or gene structure in a replicatable form.

SUMMARY OF THE INVENTION

These objects are attained in accordance with the present invention by increasing the gluconate:NADP$^+$-5-oxidoreductase gene expression in a 5-ketogluconate-producing microorganism and, in particular by increasing the gene copy number thereof. As a consequence a higher proportion of 5-ketogluconate is formed.

To increase the gene copy number of this microorganism, the gluconate-oxidoreductase gene is incorporated in a gene construct or in a vector that preferably contains regulatory gene sequences adjoining the gluconate-oxidoreductase gene and especally such regulatory gene sequences as amplify the gene expression. Then a 5-ketogluconate-producing microorganism, especially Gluconobacter or *Gluconobacter oxydans* is transformed with the gluconate-oxidoreductase-gene-containing gene construct. The host cells as will be self-understood, thus can be microorganisms which themselves did not have any gluconate:NADP$^+$-5-oxidoreductase gene originally.

The gene isolation, cloning and transformation are all effected by conventional microbiological methods. If the gene is isolated from Gluconobacter and especially *Gluconobacter oxydans*, the isolation is effected based upon the recognition of the amino acid sequence of the corresponding protein. For cloning of the gene, specific gene probes are used. The gene can be incorporated into the host cell after ligation with a vector and expression system appropriate to the host cell by standard transfer techniques and then brought to expression.

If Gluconobacter and preferably *Gluconobacter oxydans* is used for example as the host cell the preferred transformation methods are especially the biparental and triparental conjugative transfer.

After isolation and sequencing a gluconate-oxidoreductase gene is obtained with nucleotide sequencing which codes for the amino acid sequence given in Table 1 or their allel variations. Allel variations embrace especially functional derivatives containing deletions, insertions and substitutions of nucleotides which, however, retain the gluconate-oxidoreductase activity. A corresponding sequence is given in Table 1.

TABLE 1

Nucleotide Sequence of the Gene for the Gluconate:NADP$^+$-5-oxidoreductase From *G. Oxydans*

The potential ribosomal binding site is underscored, the potential terminator is marked with arrows. The amino acid sequence is shown under the corresponding nucleotide sequence. The already sequenced aminoterminal peptide sequence is underscored. Important restriction cutting sites are printed more boldly.

```
         10                      30                      50
TCACACCCAGATCTCAAAAAATCACAGACGGGACACGAGAAAAGACATACCCGAAGTCCACCTAACGTTT 70                      90                      110                     130
GTTCGCAATGAAATATCACATTTCAACAACACAAACTCTCGTTATCGATGTTACATATAACCTTCATGC 150                      170                     190
TGTCCAGAAGCGGGCGGGAAGTTTTTCTGACAAAACTTGATTGCCCGTCTGAGAGCACGCGATGCGCAC 210                      230                     250                      270
GCGGACTTGTGGATCCCTGGCGGGTTTAGGCTGCTAGGAAGAACAGAACCGTGATTTTGAAGGCTGACA
            BamHI 290                     310                     330
GATATGTCCCATCCCGATCTTTTTCTCTCCGGTGCGCGCGCCCTTGTGACCGGGGCGTCACGGGGA
        M   S   H   P   D   L   F   S   L   S   G   A   R   A   L   V   T   G   A   S   R   G 350                     370                     390                     410
ATTGGCCTGACGCTGGCAAAGGGGCTTGCGCGCTACGGGGCTGAGGTTGTCCTGAATGGCCGGAATGCT
  I   G   L   T   L   A   K   G   L   A   R   Y   G   A   E   V   V   L   N   G   R   N   A 430                     450                     470
GAAAGTCTGGACTCTGCGCAGTCCGGGTTCGAGGCGGAAGGATTGAAAGCCAGTACGGCGGTTTTCGAT
  E   S   L   D   S   A   Q   S   G   F   E   A   E   G   L   K   A   S   T   A   V   F   D 490                     510                     530                     550
GTGACGGATCAGGATGCGGTGATTGATGGCGTCGCGGCGATTGAGCGGGACATGGGACCGATCGATATC
  V   T   D   Q   D   A   V   I   D   G   V   A   A   I   E   R   D   M   G   P   I   D   I 570                     590                     610
CTGATCAATAATGCCGGGATACAGCGCCGAGCGCCTCTGGAGGAGTTTTCGCGCAAGGACTGGGATGAT
  L   I   N   N   A   G   I   Q   R   R   A   P   L   E   E   F   S   R   K   D   W   D   D 630                     650                     670                     690
CTTATGTCAACCAATGTCAACGCGGTTTTCTTCGTCGGGCAGGCGGTGGCGCGGCACATGATTCCCCGC
  L   M   S   T   N   V   N   A   V   F   F   V   G   Q   A   V   A   R   H   M   I   P   R 710                     730                     750
GGACGGGGCAAGATCGTCAATATCTGTTCCGTCCAGAGTGAACTCGCCCGTCCGGGAATTGCGCCCTAT
  G   R   G   K   I   V   N   I   C   S   V   Q   S   E   L   A   R   P   G   I   A   P   Y 770                     790                     810
ACGGCGACCAAGGGAGCGGTCAAAAACCTGACAAAAGGTATGGCGACGGACTGGGGCAGGCACGGACTT
  T   A   T   K   G   A   V   K   N   L   T   K   G   M   A   T   D   W   G   R   H   G   L 830                     850                     870                     890
CAGATCAACGGGCTGGCACCGGGGTATTTTGCGACGGAAATGACAGAAAGGCTCGTGGCCGGACGAAGAA
  Q   I   N   G   L   A   P   G   Y   F   A   T   E   M   T   E   R   L   V   A   D   E   E 910                     930                     950
TTCACGGACTGGCTGTGCAAACGGACGCCGGCAGGACGGTGGGGGCAGGTTGAGGAACTGGTCGGAGCA
  F   T   D   W   L   C   K   R   T   P   A   G   R   W   G   Q   V   E   E   L   V   G   A 970                     990                     1010                    1030
GCAGTATTTCTGTCTTCCCGGGCTTCAAGCTTCGTCAACGGGCAGGTGCTGATGGTTGATGGCGGGATA
  A   V   F   L   S   S   R   A   S   S   P   V   N   G   Q   V   L   M   V   D   G   G   I 1050                    1070                    1090
ACCGTATCGCTGTAGCCTTTCTGCAGGTGACTCTGTTTCAATTTATCAGAACTGTGTTAGGGGGCATTG
  T   V   S   L   *

1110                    1130                    1150                    1170
TCTGTCGGGTTTGTGATGGAATGGTTTTCGATAAGATGGCTTCTTATGTCGGGATGCCACAGGAAAGTT 1190                    1210                    1230
GACATTTGATGAGCTCCATCTTTGCCATCTCGCTTGCGACCGCGGCCATTGCGGCGGTTGTCATTCTTA
                                      ←—————————  —————————→

1250                    1270                    1290                    1310
TCGCCCGGTTCCGGATCAACCCGTTCATCGTCCTTTTTTCCGTCTCGATCCTGCTGGCCCTCGTTGCGG 1330                    1350                    1370
GTATGCCGGCTGACAAGGTCGTGGGGTCGTTCGAGGCGGGGGCAGGGCATGTGCTGGGGCATGTCGGAA 1390                    1410                    1430
CTGTCATCGCGCTTGGCACAATGCTTGGGAAAATGCTGGCGGAGTCCGGTGGCGCCGATCGTATCGTCC 1450                    1470                    1490                    1510
TGACGATCTGCACCCTGTCGGGTCGTCGGATATGTCGACGTACGGACTCGAATTCGTAATCAT
                                        SalI
```

Preferably regulatory gene sequences are provided adjacent the gluconate-oxidoreductase gene and which especially increase the gene activity. For example, by mutation of the regulatory gene sequences the effectivity of the binding of the regulator proteins to the DNA of the gluconate-oxidoreductase gene to be regulated can be so influenced that the transcription is thereby enhanced and thus the gene expression is augmented. Further, so-called "enhancers" can be provided adjacent the gluconate-oxidoreductase gene as regulatory sequences which give rise to increased gene expression by an improved interaction between RNA-polymerase and DNA.

Plasmids or vectors which contain the gluconate-oxidoreductase gene are obtained by cloning of the gluconate-oxodpredictase gene and are suitable for transformation of a 5-ketogluconate forming microorganism. The cells resulting from the transformation, usually Gluconobacter and especially *Gluconobacter oxydans*, contain the gene in replicatable form, i.e. in additional copies on the chromosome, whereby the gene copies are integrated at optional locations of the genome by homologous recombination and/or on a plasmid or vector.

BRIEF DESCRIPTION OF THE DRAWING

The sole FIGURE of the drawing is a diagram of which parts A–E illustrate aspects of the detailed description and Example given below.

Sequences of the amino terminus of the gluconate:NADP$^+$-5-oxidoreductase from *G. oxydans*, the PCR primer and the gno gene probe. A=Amino acid sequence of the amino terminus of the protein. B=sequences of the PCR primer. C=Nucleotide sequences of the PCR product. D=Sequence of the gene probe used. E=Restriction map of the chromosomal regions around the gno gene.

DETAILED DESCRIPTION AND EXAMPLE

Determination of the Enzymatic Activity

In the enzymatically catalyzed oxidation of gluconate to 5-ketogluconate, NADP$^+$ is reduced to NADPH which is photometrically detected (Okamoto, K., 1963, Enzymatic Studies on the Formation of 5-ketogluconic acid by *Acetobacter suboxydans*, 53, 448–452).

Product Determination

The quantitative analysis of gluconate and 5-ketogluconate is effected by HPLC (R. Klasen et al. 1992, Incapability of *Gluconobacter oxydans* to Produce Tartaric Acid, *Biotechnol. Bioeng.* 40: 183–186).

Purification of the Gluconate:NADP$^+$-5-oxidoreductase

Anion ion exchanger

Cell-free extracts of *G. oxydans* are applied to an anion ion exchanger (DEAE-Tentakel, Merck Darmstadt, Germany; 5ø 15 cm) and bonded thereto. The enzyme was eluted with an increasing NaCl gradient (0 to 500 mM) at 350 mM NaCl. The active fractions are combined and dialyzed with an ultrafiltration unit (Amicon; Cut-off: 10 kDa).

Dye Affinity Chromatography

The dialyzed enzyme solution is applied to a dye affinity column (Blue Sepharose CL-6B™, 2.6ø 20 cm; T. Atkinson et al., 1981, Triazine-dye Affinity Chromatography, *Biochem. Soc. Trans.* 9, 10–13) and bound thereto. The enzyme was eluted with an increasing NaCl gradient (0–500 mM) at 300 mM NaCl. The active fractions were combined and dialyzed with an ultrafiltration unit (Amicon; Cut-off: 10 kDa) against 25 mM histidine/HCl buffer pH 5.6.

Chromatofocussing I

The dialyzed enzyme solution was applied onto a Mono-P™ chromatography column (Pharmacia, Freiburg, Germany; 0.5ø 20 cm) equilibrated with 25 mM histidine/HCl buffer pH=5.6. The adjustment of the pH gradient and the elution of the protein were effected by application of 50 ml polybuffer PB74 (Pharmacia, Freiburg, Germany) pH=4.0 to the column.

Gel Filtration

The combined active fractions were applied to a gel filtration column (Sephacryl-S100 HR, Pharmacia, Freiburg, Germany, 2.6ø 100 cm). The elution was effected isocratically (without a gradient). The active fractions were combined and dialyzed with an ultrafiltration unit (Amicon; Cut-off: 10 kDa) against 2.5 mM acetate/NaOH buffer pH 4.8.

Chromatofocussing II

The protein solutions were applied to a Mono-P™ chromatography column (Pharmacia, Freiburg, Germany; 0.5ø 20 cm) equilibrated with 25 mM acetate/NaOH buffer pH=4.8. By application of 50 ml Polybuffer PB74 (Pharmacia, Freiburg, Germany) a pH gradient is established at the column and the protein is eluted. After testing for purity by SDS-PAGE, the purified protein is aliquoted, shock frozen in liquid nitrogen and stored at −70° C.

Amino Terminal Sequencing

For the amino terminal sequencing, 100 µg of purified protein was transferred to a PVDF membrane and investigated with a gas-phase sequencer (Appl. Biosystems, Model 470A; P. Edman et al., 1967, A Protein Sequenator, *Eur. J. Biochem.* 1: 80–91). The detection of the split off amino acid derivative (phenylthiohydantoin) was effected by HPLC.

Production of the Gene Probe

A molecular biological work required herein, unless described otherwise, is carried out according to T. Maniatis et al, 1989, Molecular Cloning: A Laboratory Manual, 2nd Edition, Cold Spring Harbour Laboratory, Cold Spring Harbour, N.Y.

The amino acids 2 through 18 of the gluconate:NADP$^+$-5-oxidoreductase were determined by Edman sequencing (see the listing A of the FIGURE). After the translation of the protein sequence into the corresponding nucleic acid sequence, taking into consideration the degeneration of the genetic code, one obtains a highly degenerated DNA sequence. For the construction of a gno-gene probe, PCR-primer is synthesized corresponding to the ends of the determined peptide sequence (see the listing B of the FIGURE).

Restriction intersections for the enzymes EcoRI and SacI are hung on at the 5'-ends of the primer in order to achieve a higher selectivity for the later cloning. After the isolation of the primer, it is used as the matrix for a PCR reaction with purefied chromosomal DNA from *G. oxydans* (Y. Takeda et al., 1991, Cloning and Sequencing of the Gene Encoding Cytochrome c-553 (CO) from *Gluconobacter oxydans, J. Ferment. Bioeng.* 72: 1–6), see S. J. Gould et al., 1989, Use of the Polymerase Chain Reaction for Homology Probing: Isolation of partial cDNA or genomic clonesencoding the iron-sulfur protein of succinate dehydrogenase from several species, *Proc. Natl. Acad. Sci. USA,* 86: 1934–1938.

A 66 bp fragment was isolated after preparative 4% agarose gel electrophoresis and cut with the restriction endonucleases EcoRI and SacI. After ligation of the previously prepared fragments with the correspondingly cut plasmid oUC19, cloning is carried out in *E. coli.* The 66 bp PCR fragment was sequenced to obtain a nondegenerate DNA sequence coding for the amino terminal of the protein. The DNA sequence can be read from the peptide sequence obtained (see the listing C of the FIGURE). From the sequenced PCR fragment a region is obtained with a length of 45 bp corresponding to the GC content of *G. oxydans* (60–65%, J. de Ley et al, 1970, The Status of the Generic Name Gluconobacter, *Int. J. Syst. Bact.* 20: 83–95). This sequence was used as a pattern for the synthesis of a gno-gene probe (see the listing D of the FIGURE).

Plotting of a Restriction Map for the Gno-gene

On the basis of the results of the PCR experiments a gno-probe is constructed and after digoxigenin marking (G. G. Schmitz et al., 1991, Non-radioactive Labeling of Oligonucleotides in vitro with the Hapten Digoxigenin by Tailing with Terminal Transferase, Anal. Biochem. 192: 222–231) is used in Southern Blot mapping (E. M. Southern, 1975, Detection of Specific Sequences Among DNA Fragments Separated by Gel Electrophoresis, J. Mol. Biol. 8: 503–517). For this purpose, chromosomal DNA from *G. oxydans* is cut with different combinations of restriction endonucleases and after separation of the restriction material, can be transferred by agarose gel electrophoresis to a nylon membrane. After hybridization with the gene probe, each cut gives only one clear signal. By calculation of the sizes of the hybridization fragments, the restriction map is obtained (see the listing E of the FIGURE).

Cloning of the Gno-gene

After producing a partial *G. oxydans* gene bank, a 3.4 kb BamHI fragment, which carries the entire gno-gene, is cloned by colony hybridization (M. Grunstein et al., 1975, Colony Hybridization: A method for the Isolation of Cloned DNA's that Contain a Specific Gene. *Proc. Natl. Acad. Sci. USA* 72: 3961–3965)

Sequencing of the Gno-gene

The sequencing of the chromosomal region of the gno-gene (F. Sanger et al., 1977, DNA Sequencing with Chain Termination Inhibitors. *Proc. Natl. Acad. Sci. USA* 74: 5463–5467) yields a nucleotide sequence of 1510 bp with an open read raster of 771 bp, that codes for a polypeptide with 257 amino acids with a molecular weight of 27,300 (Table 1). The nucleotide sequence has a ribosomal binding site 10 bp ahead of the start codon (J. Shine et al., 1974. The 3'-Terminal Sequence of *Escherichia coli* 16S Ribosomal RNA: Complementarity to Nonsense Triplets and Ribosome Binding Sites. *Proc. Natl. Acad. Sci. USA* 71: 1342–1346) and a terminator-typical palindromic structure 160 bp behind the stop codon (M. Rosenberg et al., 1979. Regulatory Sequences Involved in the Promotion and Termination of RNA Transcription. *Annu. Rev. Genet.* 13: 319–353). From the determined aminoacid sequence the peptide sequence is obtained from the protein sequencing.

Expression of the Gno-gene in *G. Oxydans*

A derivative of the plasmid RSF1010 is selected as the vector DNA for *G. oxydans* since the replicon on this plasmid enables replication of the DNA in a broad spectrum gram-negative bacterium (U. B. Priefer et al., 1985. Extension of the Host Range of *Escherichia coli* Vectors by Incorporation of RSF 1010 Replication and Mobilization Functions. *J. Bacteriol.* 163: 324–330). The plasmid pRS201P$_R$ was used as the basis for further investigations of gene transfer in *G. oxydans* (R. Schröder et al., 1991. Expression of the Core Antigen of Hepatitus B virus (HBV) in *Acetobacter methanolicus* Using Broad-Host-Range Vectors. *Appl. Microbiol. Biotechnol.* 35: 631–637). The plasmid transfer is effected by conjugation (C. Comdon et al., 1991. Conjugation and Heterologous Gene Expression in *Gluconobacter oxydans* ssp. suboxydans. *FEMS Microbiol. Lett.* 80: 173–179). The plasmid pRS201P$_R$ contains, apart from the promoter, also the gene for a temperature-sensitive derivative of the cI repressor (cI857), which regulates the promoter. To deregulate the promoter, a part of the cI857-repressor of the plasmid pRS201P$_R$ is eliminated (pRS201P). A 1.25 kbp BamHI/SalI fragment coding for the gluconate:NADP$^+$-5-oxidoreductase is ligated with correspondingly restrung pRS201P$_R$ and pRS201P. The plasmids pRS201P$_R$-gno and pRS201P-gno are translated on *G. oxydans* by conjugation. The activity determination indicated that a 6.5 to 85-times increase in the gluconate:NADP$^+$-5-oxidoreductase activity was present in the recombinant *G. oxydans* strains (Table 2).

TABLE 2

Expression of the gno-gene in *G. oxydans* DSM 3503 under control of the λ promoters in the plasmids pRS201P$_R$-gno and pRS201P-gno and the resulting gluconate:NADP$^+$-5-oxidoreductase activity.

The Enzymatic activity is determined after 20 h incubation at 30° C.

| Strain | Enzymatic Activity |
|---|---|
| G. oxydans | 0.08 |
| G. oxydanspRS201PR | 0.08 |
| G. oxydanspRS201P | 0.08 |
| G. oxydanspRS201P$_R$-gno | 0.52 |
| G. oxydanspRS201P-gno | 6.8 |

5-Ketogluconate Productivity of the Recombinant Strain

To determine the 5-ketogluconate productivity, the recombinant *G. oxydans* strains were investigated as to the accumulation of 5-ketogluconate in a fermentation medium (U. Kotera et al., 1972. Isolation and Chemical structure of New Oxidation pathway from glucose to tartaric acid Through this New Compound. Agric. Biol. Chem. 36: 1315–1325). Samples were taken daily for the metabolite determination and quantitatively evaluated by HPLC measurements. The results show an increase in the 5-ketogluconate formation of 11% by superexpression of the gno-gene (*G. oxidans* pRS201P$_R$-gno) by comparison to the strains with the gluconate:NADP$^+$-5-oxidoreductase activity of the wild type (*G. oxydans* wt, *G. oxydans* pRS201P), see Table 3.

TABLE 3

Conversion of glucose to 5-ketogluconate by recombinant *G. oxydans* strains.

Incubation was effected in a mineral salt medium with 10% (w/v) glucose.

| Strain | Period [d] | 5-Ketogluconate [mM] |
|---|---|---|
| G. oxydans wt | 1 | 15 |
|  | 2 | 56 |
|  | 3 | 71 |
| G. oxydans pRS201P | 1 | 12 |
|  | 2 | 58 |
|  | 3 | 69 |
| G. oxydans PRS201P-gno | 1 | 19 |
|  | 2 | 66 |
|  | 3 | 79 |

We claim:

1. A method of making 5-ketogluconate, which comprises the steps of:
   (a) transforming a microorganism with a vector containing a gene sequence encoding the amino acid sequence of Seq. ID No. 7 or a fragment thereof having gluconate:NADP-5-oxidoreductase activity;
   (b) culturing said microorganism in a medium containing gluconate to produce 5-ketogluconate; and
   (c) recovering 5-ketogluconate from said medium.

2. A method of making 5-ketogluconate, which comprises the steps of:
   (a) transforming a microorganism with a vector containing a gene sequence that is Seq. ID No. 6 or a fragment thereof encoding the amino acid sequence of Seq. ID No. 7 or a fragment thereof having gluconate:NADP-5-oxidoreductase activity;
   (b) culturing said microorganism in a medium containing gluconate to produce 5-ketogluconate; and
   (c) recovering 5-ketogluconate from said medium.

3. An isolated gluconate: NADP-5-oxidoreductase gene having the nucleic acid sequence given in Seq. ID No. 6 or a fragment thereof encoding gluconate:NADP-5-oxidoreductase activity.

4. The method defined in claim 2 wherein the microorganism producing 5-keto-gluconate is a Gluconobacter.

5. The method defined in claim 4 wherein the Gluconobacter is *Gluconobacter oxydans*.

6. The method defined in claim 2 wherein the gene sequence is isolated from a Gluconobacter.

7. The method defined in claim 2 wherein the gene sequence is isolated from *Gluconobacter oxydans*.

8. A gene construct containing the isolated gluconate:NADP-5-oxidoreductase gene having the nucleic acid sequence given in Seq. ID No. 6 or a fragment thereof encoding gluconate:NADP-5-oxidoreductase activity as defined in claim 3.

9. A vector containing the isolated gluconate:NADP-5-oxidoreductase gene having the nucleic acid sequence given in Seq. ID No. 6 or a fragment thereof encoding NADP-5-oxidoreductase activity as defined in claim 3.

10. A transformed cell containing an isolated gluconate:NADP-5-oxidoreductase gene having the nucleic acid sequence given in Seq. ID No. 6 or a fragment thereof encoding gluconate:NADP-5-oxidoreductase activity as defined in claim 3.

11. The transformed cell defined in claim 10 which is a Gluconobacter.

12. The transferred cell defined in claim 11 wherein the Gluconobacter is *Gluconobacter oxydans*.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..51

( x ) SEQUENCE DESCRIPTION: SEQ ID NO:1:

```
CAT  CCC  GAT  CTG  TTC  TCT  CTC  TCC  GGT  GCG  CGC  GCC  CTC  GTC  ACC  GGA        48
His  Pro  Asp  Leu  Phe  Ser  Leu  Ser  Gly  Ala  Arg  Ala  Leu  Val  Thr  Gly
  1                    5                        10                       15

GCT                                                                                   51
Ala
```

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
His  Pro  Asp  Leu  Phe  Ser  Leu  Ser  Gly  Ala  Arg  Ala  Leu  Val  Thr  Gly
  1                    5                        10                       15

Ala
```

( 2 ) INFORMATION FOR SEQ ID NO:3:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

```
CATCCCGATC  TGTTCTCTCT  CTCCGGTGCG  CGCGCCCTCG  TCACC           45
```

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GCGAATTCCA TCCCGATCTG TTCTC  25

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

CGGGAGCAGT GGCCACGCTC GAGCG  25

( 2 ) INFORMATION FOR SEQ ID NO:6:

( i ) SEQUENCE CHARACTERISTICS:
        ( A ) LENGTH: 1512 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 280..1050

( x i ) SEQUENCE DESCRIPTION: SEQ ID NO:6:

```
TCACACCCAG ATCTCAAAAA TCACAGACGG GACACGAGAA AAGACATACC CGAAGTCCAC        60

CTAACGTTTG TTCGCAATGA AATATCACAT TTCAACAACA CAAACTCTCG TTATCGATGT       120

TACATATAAC CTTCATGCTG TCCAGAAGCG GGCGGAAGT TTTTCTGACA AAACTTGATT        180

GCCCGTCTGA GAGCACGCGA TGCGCACGCG GACTTGTGGA TCCCTGGCGG GTTTAGGCTG       240

CTAGGAAGAA CAGAACCGTG ATTTTGAAGG CTGACAGAT ATG TCC CAT CCC GAT          294
                                             Met Ser His Pro Asp
                                              1               5

CTT TTT TCT CTC TCC GGT GCG CGC GCC CTT GTG ACC GGG GCG TCA CGG         342
Leu Phe Ser Leu Ser Gly Ala Arg Ala Leu Val Thr Gly Ala Ser Arg
            10                  15                  20

GGA ATT GGC CTG ACG CTG GCA AAG GGG CTT GCG CGC TAC GGG GCT GAG         390
Gly Ile Gly Leu Thr Leu Ala Lys Gly Leu Ala Arg Tyr Gly Ala Glu
            25                  30                  35

GTT GTC CTG AAT GGC CGG AAT GCT GAA AGT CTG GAC TCT GCG CAG TCC         438
Val Val Leu Asn Gly Arg Asn Ala Glu Ser Leu Asp Ser Ala Gln Ser
        40                  45                  50

GGG TTC GAG GCG GAA GGA TTG AAA GCC AGT ACG GCG GTT TTC GAT GTG         486
Gly Phe Glu Ala Glu Gly Leu Lys Ala Ser Thr Ala Val Phe Asp Val
    55                  60                  65

ACG GAT CAG GAT GCG GTG ATT GAT GGC GTC GCG GCG ATT GAG CGG GAC         534
Thr Asp Gln Asp Ala Val Ile Asp Gly Val Ala Ala Ile Glu Arg Asp
```

```
                70                      75                      80                      85
ATG  GGA  CCG  ATC  GAT  ATC  CTG  ATC  AAT  AAT  GCC  GGG  ATA  CAG  CGC  CGA            582
Met  Gly  Pro  Ile  Asp  Ile  Leu  Ile  Asn  Asn  Ala  Gly  Ile  Gln  Arg  Arg
               90                      95                     100

GCG  CCT  CTG  GAG  GAG  TTT  TCG  CGC  AAG  GAC  TGG  GAT  GAT  CTG  ATG  TCA            630
Ala  Pro  Leu  Glu  Glu  Phe  Ser  Arg  Lys  Asp  Trp  Asp  Asp  Leu  Met  Ser
              105                     110                     115

ACC  AAT  GTC  AAC  GCG  GTT  TTC  TTC  GTC  GGG  CAG  GCG  GTG  GCG  CGG  CAC            678
Thr  Asn  Val  Asn  Ala  Val  Phe  Phe  Val  Gly  Gln  Ala  Val  Ala  Arg  His
          120                     125                     130

ATG  ATT  CCC  CGC  GGA  CGG  GGC  AAG  ATC  GTC  AAT  ATC  TGT  TCC  GTC  CAG            726
Met  Ile  Pro  Arg  Gly  Arg  Gly  Lys  Ile  Val  Asn  Ile  Cys  Ser  Val  Gln
     135                     140                     145

AGT  GAA  CTC  GCC  CGT  CCG  GGA  ATT  GCG  CCC  TAT  ACG  GCG  ACC  AAG  GGA            774
Ser  Glu  Leu  Ala  Arg  Pro  Gly  Ile  Ala  Pro  Tyr  Thr  Ala  Thr  Lys  Gly
150                     155                     160                     165

GCG  GTC  AAA  AAC  CTG  ACA  AAA  GGT  ATG  GCG  ACG  GAC  TGG  GGC  AGG  CAC            822
Ala  Val  Lys  Asn  Leu  Thr  Lys  Gly  Met  Ala  Thr  Asp  Trp  Gly  Arg  His
                    170                     175                     180

GGA  CTT  CAG  ATC  AAC  GGG  CTG  GCA  CCG  GGG  TAT  TTT  GCG  ACG  GAA  ATG            870
Gly  Leu  Gln  Ile  Asn  Gly  Leu  Ala  Pro  Gly  Tyr  Phe  Ala  Thr  Glu  Met
               185                     190                     195

ACA  GAA  AGG  CTC  GTG  GCG  GAC  GAA  GAA  TTC  ACG  GAC  TGG  CTG  TGC  AAA            918
Thr  Glu  Arg  Leu  Val  Ala  Asp  Glu  Glu  Phe  Thr  Asp  Trp  Leu  Cys  Lys
          200                     205                     210

CGG  ACG  CCG  GCA  GGA  CGG  TGG  GGG  CAG  GTT  GAG  GAA  CTG  GTC  GGA  GCA            966
Arg  Thr  Pro  Ala  Gly  Arg  Trp  Gly  Gln  Val  Glu  Glu  Leu  Val  Gly  Ala
     215                     220                     225

GCA  GTA  TTT  CTG  TCT  TCC  CGG  GCT  TCA  AGC  TTC  GTC  AAC  GGG  CAG  GTG           1014
Ala  Val  Phe  Leu  Ser  Ser  Arg  Ala  Ser  Ser  Phe  Val  Asn  Gly  Gln  Val
230                     235                     240                     245

CTG  ATG  GTT  GAT  GGC  GGG  ATA  ACC  GTA  TCG  CTG  TAG  CCTTTCTGCA                    1060
Leu  Met  Val  Asp  Gly  Gly  Ile  Thr  Val  Ser  Leu
                    250                     255

GGTGACTCTG   TTTCAATTTA   TCAGAACTGT   GTTAGGGGGC   ATTGTCTGTC   GGGTTTGTGA              1120

TGGAATGGTT   TTCGATAAGA   TGGCTTCTTA   TGTCGGGATG   CCACAGGAAA   GTTGACATTT              1180

GATGAGCTCC   ATCTTTGCCA   TCTCGCTTGC   GACCGCGGCC   ATTGCGGCGG   TTGTCATTCT              1240

TATCGCCCGG   TTCCGGATCA   ACCCGTTCAT   CGTCCTTTTT   TCCGTCTCGA   TCCTGCTGGC              1300

CCTCGTTGCG   GGTATGCCGG   CTGACAAGGT   CGTGGGGTCG   TTCGAGGCGG   GGGCAGGGCA              1360

TGTGCTGGGG   CATGTCGGAA   CTGTCATCGC   GCTTGGCACA   ATGCTTGGGA   AAATGCTGGC              1420

GGAGTCCGGT   GGCGCCGATC   GTATCGTCCT   GACGATCTGC   ACCCTGTCGG   GTCGTCGGAT              1480

ATGTCGACGT   ACGGACTCGA   ATTCGTAATC   AT                                                1512
```

( 2 ) INFORMATION FOR SEQ ID NO:7:

( i ) SEQUENCE CHARACTERISTICS:
        ( A ) LENGTH: 256 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Ser  His  Pro  Asp  Leu  Phe  Ser  Leu  Ser  Gly  Ala  Arg  Ala  Leu  Val
  1                 5                      10                     15

Thr  Gly  Ala  Ser  Arg  Gly  Ile  Gly  Leu  Thr  Leu  Ala  Lys  Gly  Leu  Ala
               20                      25                     30
```

-continued

| | | | | | | | | | | | | | | | |
|---|---|---|---|---|---|---|---|---|---|---|---|---|---|---|---|
| Arg | Tyr | Gly | Ala | Glu | Val | Val | Leu | Asn | Gly | Arg | Asn | Ala | Glu | Ser | Leu |
| | | 35 | | | | | 40 | | | | | 45 | | | |
| Asp | Ser | Ala | Gln | Ser | Gly | Phe | Glu | Ala | Glu | Gly | Leu | Lys | Ala | Ser | Thr |
| | | 50 | | | | 55 | | | | | 60 | | | | |
| Ala | Val | Phe | Asp | Val | Thr | Asp | Gln | Asp | Ala | Val | Ile | Asp | Gly | Val | Ala |
| 65 | | | | | 70 | | | | | 75 | | | | | 80 |
| Ala | Ile | Glu | Arg | Asp | Met | Gly | Pro | Ile | Asp | Ile | Leu | Ile | Asn | Asn | Ala |
| | | | | 85 | | | | | 90 | | | | | 95 | |
| Gly | Ile | Gln | Arg | Arg | Ala | Pro | Leu | Glu | Glu | Phe | Ser | Arg | Lys | Asp | Trp |
| | | | 100 | | | | | 105 | | | | | 110 | | |
| Asp | Asp | Leu | Met | Ser | Thr | Asn | Val | Asn | Ala | Val | Phe | Phe | Val | Gly | Gln |
| | | 115 | | | | | 120 | | | | | 125 | | | |
| Ala | Val | Ala | Arg | His | Met | Ile | Pro | Arg | Gly | Arg | Gly | Lys | Ile | Val | Asn |
| | 130 | | | | | 135 | | | | | 140 | | | | |
| Ile | Cys | Ser | Val | Gln | Ser | Glu | Leu | Ala | Arg | Pro | Gly | Ile | Ala | Pro | Tyr |
| 145 | | | | | 150 | | | | | 155 | | | | | 160 |
| Thr | Ala | Thr | Lys | Gly | Ala | Val | Lys | Asn | Leu | Thr | Lys | Gly | Met | Ala | Thr |
| | | | | 165 | | | | | 170 | | | | | 175 | |
| Asp | Trp | Gly | Arg | His | Gly | Leu | Gln | Ile | Asn | Gly | Leu | Ala | Pro | Gly | Tyr |
| | | | 180 | | | | | 185 | | | | | 190 | | |
| Phe | Ala | Thr | Glu | Met | Thr | Glu | Arg | Leu | Val | Ala | Asp | Glu | Glu | Phe | Thr |
| | | 195 | | | | | 200 | | | | | 205 | | | |
| Asp | Trp | Leu | Cys | Lys | Arg | Thr | Pro | Ala | Gly | Arg | Trp | Gly | Gln | Val | Glu |
| | 210 | | | | | 215 | | | | | 220 | | | | |
| Glu | Leu | Val | Gly | Ala | Ala | Val | Phe | Leu | Ser | Ser | Arg | Ala | Ser | Ser | Phe |
| 225 | | | | | 230 | | | | | 235 | | | | | 240 |
| Val | Asn | Gly | Gln | Val | Leu | Met | Val | Asp | Gly | Gly | Ile | Thr | Val | Ser | Leu |
| | | | | 245 | | | | | 250 | | | | | 255 | |